United States Patent
Strauss et al.

(10) Patent No.: US 8,642,055 B2
(45) Date of Patent: Feb. 4, 2014

(54) FREE-FLOWING EMULSION CONCENTRATES

(75) Inventors: Gabriele Strauss, Düsseldorf (DE); Rolf Kawa, Monheim (DE); Anja Stork, Köln (DE); Petra Schulte, Köln (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/143,564

(22) PCT Filed: Dec. 23, 2009

(86) PCT No.: PCT/EP2009/009252
§ 371 (c)(1), (2), (4) Date: Jul. 7, 2011

(87) PCT Pub. No.: WO2010/078946
PCT Pub. Date: Jul. 15, 2010

(65) Prior Publication Data
US 2012/0027826 A1    Feb. 2, 2012

(30) Foreign Application Priority Data
Jan. 8, 2009 (EP) .................................. 09000134

(51) Int. Cl.
*A61K 8/02* (2006.01)

(52) U.S. Cl.
USPC ...................................................... 424/401

(58) Field of Classification Search
None
See application file for complete search history.

(56) References Cited

U.S. PATENT DOCUMENTS

| | | |
|---|---|---|
| 5,494,938 A | 2/1996 | Kawa et al. |
| 5,705,169 A | 1/1998 | Stein et al. |
| 5,730,960 A | 3/1998 | Stein et al. |
| 7,358,279 B2 * | 4/2008 | Goget et al. ............... 424/70.13 |

FOREIGN PATENT DOCUMENTS

| | | |
|---|---|---|
| DE | 19712033 | 9/1998 |
| EP | 0693471 | 1/1996 |
| EP | 0694521 | 1/1998 |
| EP | 0818450 | 1/1998 |
| EP | 1371359 | 12/2003 |
| WO | WO 92/07543 | 5/1992 |
| WO | WO 2006/000360 | 1/2006 |
| WO | WO 2008/019773 | 2/2008 |

OTHER PUBLICATIONS

"Commission Directive 2005/9/EC", *Official Journal of the European Union* Jan. 28, 2005, 2 pgs.
"DIN 55 943—Farbmittel—Begriffe", Oct. 2001, 20 pgs.
"DIN 55 944—Farbittel—Einteilung nach koloristichen und chemischen Gesichtspunkten", Nov. 2003, 1-17.
"DIN 55 944—Farbmittel—Einteilung nach koloristischen und chemischen Gasichtspunkten", Apr. 1990, 1-12.
"Machine Translation of DE19712033", Jun. 28, 2011, 17 pgs.
"Machine Translation of EP0818450", Jun. 28, 2011, 17 pgs.
"Machine Translation of EP1371359",Jun. 28, 2011, 43 pgs.
"Machine Translation of WO 2008/019773", Jun. 28, 2011, 19 pgs.
"PCT international Search Report for PCT/EP2009/009252", Feb. 19, 2010, 2 pgs.
Finkel, P., "Formulierung kosmetischer Sonnenschutzmittel", *Parfümerie und Kosmetik*, 80 Mar. 1999, 10-16.
Finkel, P., "Formulierung kosmetischer Sonnenschutzmittel", *SOFW-Journal*, 122 Aug. 1996, 543-548.

\* cited by examiner

*Primary Examiner* — Anand Desai
*Assistant Examiner* — Melissa Mercier
(74) *Attorney, Agent, or Firm* — Servilla Whitney LLC

(57) ABSTRACT

Emulsion concentrates comprising at least one alkyl and/or alkenyl oligoglycoside having 6 to 22 carbon atoms in the alk(en)yl radical, polyglycerol esters, at least one polyol, at least one glyceride having a melting point greater than or equal to 20° C., at least one oil component liquid at 20° C. and with a polarity of more than 30-40 mN/m and at least one oil component liquid at 20° C. and with a polarity of 5-30 mN/m are described. Methods of making and using such emulsion concentrates are also described. Articles employing the emulsion concentrates are also described.

19 Claims, No Drawings

FREE-FLOWING EMULSION CONCENTRATES

CROSS-REFERENCE TO RELATED APPLICATIONS

This application is a National Phase entry of International Application No. PCT/EP2009/009252, filed Dec. 23, 2009, which claims priority of European Patent Application No. 09000134, filed Jan. 8, 2009, the entire disclosures of which are hereby incorporated by reference in their entirety.

BACKGROUND

The present invention relates to emulsion concentrates that are free-flowing and pumpable at low temperatures and which have good sensory properties and good storage stability, and which are suitable in particular for cosmetic wipes, and in which it is possible to dispense with the use of ethoxylated raw materials.

Emulsion concentrates on the market are generally based on ethoxylated raw materials, which are regarded as critical from an ecological point of view.

For EO-free (i.e. free from ethoxylated raw materials), hydrophilic emulsion concentrates, a combination is known which is based on water-insoluble oil components, emulsifiers and polyols and is available e.g. under the name Emulgade® CPE (trade name). A disadvantage with these emulsion concentrates is their viscosity increase at low temperatures, particularly at temperatures below 15° C. and their sensory properties.

WO 2008/019773 A1 describes emulsion concentrates with water-insoluble components, hydrophilic nonionic emulsifiers, lipophilic coemulsifiers, polyols and water. Here, emulsifiers based on ethoxylated substances are used. Furthermore, a free-flowability and pumpability of the emulsion concentrates at room temperature is stated, which can preferably be produced with small fractions of ethoxylated substances/raw materials. It was of particular interest to provide emulsion concentrates which can be produced without ethoxylated substances.

It was an object of the present invention to provide emulsion concentrates which are free-flowing and pumpable at temperatures below 15° C. and have good sensory properties. According to the invention, free-flowing and pumpable are terms used to refer to emulsion concentrates whose viscosity at 15° C. is below 30,000 mPa*s, measured using a Brookfield rotary viscometer (model RVF, spindle 5, 10 rpm, 23° C.)

These emulsion concentrates can be applied neat to substrates, but are normally diluted. In the simplest case, the dilution takes place with water. It is a further object of the invention to provide emulsion concentrates which are storage-stable after dilution, which is generally ensured if the particle size, measured using a Coulter LS, is less than 100 nm and the dilutions are transparent and do not separate.

SUMMARY

One or more embodiments of the invention are directed to emulsion concentrates. The emulsion concentrations comprise (A) at least one alkyl and/or alkenyl oligoglycoside having 6 to 22 carbon atoms in the alk(en)yl radical, (B) polyglycerol ester, (C) at least one polyol, (D) at least one glyceride having a melting point greater than or equal to 20° C.; (E) at least one oil component liquid at 20° C. and with a polarity of more than 30-40 mN/m and (F) at least one oil component liquid at 20° C. and with a polarity of 5-30 mN/m. Components (A), (B) and (C) have a weight ratio A:B:C of 1:(0.6-0.8):(0.9-1.1). Components (A) and (D) have a weight ratio A:D of from 4:1 to 1.5:1. Components (E) and (F) have a weight ratio E:F of from 1:1 to 1:3. The water fraction is less than or equal to 20% by weight, based on the total weight of the emulsion concentrate.

In some embodiments, the at least one alkyl and/or alkenyl oligoglycoside have a general formula (I)

$$G_m\text{-}R^1 \qquad (I)$$

where G is a sugar radical having 5 or 6 carbon atoms, R1 is a C6 to C22 alkyl and/or alkenyl radical in acetal bond and m is an average value from 1 to 10. In detailed embodiments, m has an average value from 1.2 to 1.8.

In some embodiments, the polyglycerol ester is a polyglycerol ester of a polyhydroxystearic acid. In detailed embodiments, the at least one polyol has 2 to 6 hydroxyl groups. In specific embodiments, the polyol has 2 to 18 carbon atoms.

In one or more embodiments, the at least one glyceride comprises glycerides of C18 fatty acids. In detailed embodiments, the glycerides of C18 fatty acids have a fraction of glycerol monoester greater than or equal to 90% by weight based on the weight of all of the glycerides of C18 fatty acids.

In some embodiments, there is less than 10% by weight ethoxylated substances. In specific embodiments, there is less than 5% by weight ethoxylated substances.

In one or more embodiments, the emulsion concentrate has a viscosity at 15° C. of less than 30,000 mPa*s.

Additional embodiments of the invention are directed to cosmetic or pharmaceutical preparations comprising the emulsion concentrate described herein.

Further embodiments of the invention are directed to methods of making a cosmetic or pharmaceutical preparation. The methods comprise an oil-in-water emulsion including the emulsion concentrate described.

Some embodiments of the invention are directed to cosmetic or pharmaceutical preparations comprising the emulsion concentrate described.

Additional embodiments are directed to methods of treating a substrate comprising applying the emulsion concentrate described to the substrate.

One or more embodiments of the invention are directed to a substrate. The substrate comprises (A) at least one alkyl and/or alkenyl oligoglycoside having 6 to 22 carbon atoms in the alk(en)yl radical, (B) polyglycerol ester, (C) at least one polyol, (D) at least one glyceride having a melting point greater than or equal to 20° C.; (E) at least one oil component liquid at 20° C. and with a polarity of more than 30-40 mN/m and (F) at least one oil component liquid at 20° C. and with a polarity of 5-30 mN/m. Components (A), (B) and (C) have a weight ratio A:B:C of 1:(0.6-0.8):(0.9-1.1), components (A) and (D) have a weight ratio A:D of from 4:1 to 1.5:1. Components (E) and (F) have a weight ratio E:F of from 1:1 to 1:3. The water fraction is less than or equal to 20% by weight, based on the total weight of the emulsion concentrate. In detailed embodiments, the substrate is paper, a nonwoven product or a woven product.

Additional embodiments of the invention are directed to methods of bodycare or cleansing comprising using the substrate described.

Additional embodiments of the invention are directed to an article comprising a substrate with an emulsion concentrate thereon. The emulsion concentrate comprises (A) at least one alkyl and/or alkenyl oligoglycoside having 6 to 22 carbon atoms in the alk(en)yl radical, (B) polyglycerol ester, (C) at least one polyol, (D) at least one glyceride having a melting point greater than or equal to 20° C.; (E) at least one oil component liquid at 20° C. and with a polarity of more than 30-40 mN/m and (F) at least one oil component liquid at 20° C. and with a polarity of 5-30 mN/m. Components (A), (B) and (C) are present in a weight ratio A:B:C of 1:(0.6-0.8):(0.9-1.1). Components (A) and (D) are present in a weight ratio A:D of from 4:1 to 1.5:1. Components (E) and (F) are present in a weight ratio E:F of from 1:1 to 1:3. The water fraction is less than or equal to 20% by weight, based on the total weight of the emulsion concentrate.

In specific embodiments, the emulsion concentrate is part of an oil-in-water emulsion.

DETAILED DESCRIPTION

Surprisingly, it has been found that emulsion concentrates of the present invention solve these problems. The term emulsion concentrate is used synonymously with the term concentrate.

The present invention provides an emulsion concentrate comprising the following components:
(A) alkyl and/or alkenyl oligoglycoside(s) having 6 to 22 carbon atoms in the alk(en)yl radical,
(B) polyglycerol ester,
(C) polyol(s),
(D) glyceride(s) which have a melting point greater than or equal to 20° C.
(E) oil component(s) liquid at 20° C. and with a polarity of more than 30-40 mN/m and
(F) oil component(s) liquid at 20° C. and with a polarity of 5-30 mN/m,
where
   the components (A), (B) and (C) have a weight ratio A:B:C of 1:(0.6-0.8):(0.9-1.1),
   the components (A) and (D) have a weight ratio A:D of from 4:1 to 1.5:1,
   the components (E) and (F) have a weight ratio E:F of from 1:1 to 1:3, and
   the water fraction is less than or equal to 20% by weight, based on the total weight of the emulsion concentrate.

If these conditions are observed, emulsion concentrates can be obtained which, at 15° C., have a viscosity below 30,000 mPa*s, determined by a Brookfield rotary viscometer (model RVF, spindle 5, 10 rpm, 23° C.). Preferably, the emulsion concentrates according to the invention have, at 15° C., a viscosity of below 20,000 mPa*s, further preferably below 15,000 mPa*s.

Both the emulsion concentrates according to embodiments of the invention and their dilutions have good storage stability, which is evident from the fact that, for example after 5% dilution with water, the dilutions are transparent after a week and the average particle size, determined by means of a Coulter LS, is less than 100 nm.

The present invention also relates to cosmetic and/or pharmaceutical preparations which are obtained by diluting the emulsion concentrate according to the invention.

Furthermore, the present invention relates to substrates, in particular paper, nonwoven or woven products, for bodycare and/or cleaning, such as e.g. cosmetic wipes, which comprise the emulsion concentrate or the cosmetic and/or pharmaceutical preparation.

Surprisingly, it has been found that emulsion concentrates can be prepared which are free-flowing and pumpable at low temperatures, have good sensory properties and are storage-stable without ethoxylated substances having to be used during the formulation. These effects can surprisingly be achieved in the emulsion concentrate as the result of the interaction between the components and their quantitative ratios, as stated in claim 1.

Oil Component (Components (E) and (F))

An essential feature of the present invention is the composition of the lipophilic phase with regard to components (E) and (F). It is required according to the invention that part of the lipophilic phase is formed by components with low polarity (component (F)) and part is formed by components with high polarity (component (E)).

According to some embodiments, of the invention, one part of the lipophilic phase has a polarity of 5 to 30 mN/m (component F) and another part has a polarity of more than 30-40 mN/m (component E).

Both component (E) and also component (F) are liquid at 20° C. According to the definition, components (E) and (F) are substances different from components (A), (B), (C) and (D). For calculating the ratios according to the invention of the components relative to one another, the components (A), (B), (C) and (D) are not included in components (E) and (F) even if these components have a polarity in the range of values stated for components (E) and (F).

The polarity of the oil components (E) and (F) is given via the interfacial tension. The interfacial tension is the force which acts on an imaginary line, one meter in length, located in the interface between two phases. The physical unit for the interfacial tension is conventionally calculated from the force/length relationship and is usually expressed in mN/m (millinewtons per meter). It has a positive sign if it reduces the interface; in the converse case, it has a negative sign. Relatively low positive values signify relatively high polarity. The interfacial tension is determined according to the invention in accordance with the ASTM method D971-99a (reapproved 2004).

It was unexpected that as a result of the polarity distribution according to the invention in the lipophilic phase, the free-flowability of the emulsion concentrates at lower temperatures could be improved and at the same time other advantages could be achieved, such as good sensory properties, omission of ethoxylated raw materials and storage stability.

The emulsion concentrate comprises, as component (E), oil component(s) liquid at 20° C. and having a polarity of more than 30-40 mN/m.

The content of component (E), based on the emulsion concentrate, is generally 3 to 25% by weight, preferably 5-20% by weight, even more preferably 7-15% by weight.

In one preferred embodiment of the invention, a compound selected from the group consisting of hydrocarbons, dialkyl ethers, fatty acid esters having 12-44 carbon atoms, dialkyl carbonates, Guerbet alcohols and silicone oils or mixtures thereof, provided it has the required polarity of more than 30 to 40 mN/m, is used as components (E).

Examples of suitable components (E) are, for example, the following compounds (INCI name followed by trade name of Cognis GmbH): Dicaprylyl Ether (Cetiol® OE), Dicarprylyl Carbonate (Cetiol®CC, Propylheptyl Caprylate (Cetiol®Sensoft), Hexyl Laurate (Cetiol®A), and also the substances available under the INCI name Coco caprylate and Caprylyl caprylate caprate.

The emulsion concentrate comprises, as component (F) oil component(s) liquid at 20° C. and having a polarity of 5-30 mN/m.

The content of component (F), based on the emulsion concentrate, is generally 15 to 40% by weight, preferably 20-35% by weight.

In a preferred embodiment of the invention, a compound selected from the group consisting of triglycerides, alkyl benzoates, fatty acid esters having 12-44 carbon atoms or mixtures thereof, provided it has the required polarity of 5 to 30 to 40 mN/m, is used as components (F).

Examples of suitable components (F) are, for example, the following compounds (INCI name followed by trade name of Cognis GmbH): Caprylic/Capric Triglyceride (Myrito® 312), Olus Oil (Cegesoft® PS 6), C12-15 Alkyl Benzoate (Cetiol®AB), Hexyldecanol (and) Hexyldecyl Laurate (Cetiol® PGL), Ethylhexyl Palmitate (Cegesoft® C 24) almond oil.

According to the invention, the weight ratio of components (E) and (F) relative to one another is 1:1 to 1:3.

The oil components (E) and (F) can comprise oils, fats, waxes and also any desired mixtures thereof. Suitable oil components (E) and (F) are all fatty substances or fatty substance mixtures liquid at 20° C., i.e. also mixtures of liquid fatty substances or paraffins and solid fatty substances or paraffins dissolved therein, provided these mixtures are liquid at 20° C. and have the required polarity.

"Liquid" is the term used to refer to components whose viscosity (at 20° C.) is below 20 Pas (measured using a Brookfield rotary viscometer model RVF, spindle 4, 10 rpm, 23° C.)

Examples of components of the lipophilic phase are given below. The person skilled in the art can select from this the components suitable for the invention by reference to the polarity of the components by looking up the polarity of the substances in publications or determining it as described above in accordance with the ASTM method D971-99a (reapproved 2004).

The term "oils" (used synonymously: oil component) is used to refer to water-insoluble organic compounds, liquid at 20° C., having a relatively low vapor pressure. The common feature of the oils is not their concurring chemical constitution, but their similar physical consistency.

Suitable oil components are, for example, the classes of compound specified below provided these are liquid at 20° C. Thus, for example, Guerbet alcohols based on fatty alcohols having 6 to 18, preferably 8 to 10, carbon atoms (e.g. Eutanol® G), esters of linear $C_6$-$C_{22}$-fatty acids with linear or branched $C_6$-$C_{22}$-fatty alcohols (e.g. Cetiol® Sensoft) or esters of branched $C_6$-$C_{13}$-carboxylic acids with linear or branched $C_6$-$C_{22}$-fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate, erucyl erucate and hexyldecyl stearate (Eutanol® G 16 S). Also suitable are esters of linear $C_6$-$C_{22}$-fatty acids with branched alcohols, in particular 2-ethylhexanol, esters of $C_3$-$C_{38}$-alkylhydroxycarboxylic acids with linear or branched $C_6$-$C_{22}$-fatty alcohols—in particular dioctyl malate—, esters of linear and/or branched fatty acids with polyhydric alcohols (such as e.g. propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes such as e.g. 1,3-dialkylcyclohexanes, linear and branched $C_6$-$C_{22}$-fatty alcohol carbonates, such as e.g. dicaprylyl carbonate (Cetiol®CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as e.g. dicaprylyl ether (Cetiol® OE), ring-opening products of epoxidized fatty acid esters with polyols (Hydagen® HSP, Sovermol® 750, Sovermol® 1102), silicone oils (cyclomethicones, silicon methicone types etc. and/or aliphatic or naphthenic hydrocarbons, such as e.g. like mineral oil, vaseline, petrolatum, squalane, squalene or dialkylcyclohexanes. Suitable oils are also esters of 2-propylheptanol with carboxylic acids, in particular with n-octanoic acid (e.g. Cetiol®SenSoft). Suitable oils are also short-chain, linear hydrocarbons, such as for example n-undecane, n-tridecane and n-pentadecane and mixtures thereof, in particular mixtures of n-undecane and n-tridecane.

Suitable further oil components are, for example, silicone oils. They may be present as cyclic and/or linear silicone oils. Silicone oils are high molecular weight synthetic polymeric compounds in which silicon atoms are linked via oxygen atoms in a chain-like and/or reticular manner and the remaining valences of the silicon are saturated by hydrocarbon radicals (in most cases methyl groups, less frequently ethyl, propyl, phenyl groups etc.). Systematically, the silicone oils are referred to as polyorganosiloxanes. The methyl-substituted polyorganosiloxanes, which are the most important compounds of this group in terms of amount and are characterized by the following structural formula

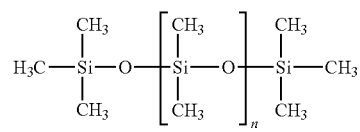

are also referred to as polydimethylsiloxane or dimethicone (INCI). Dimethicones come in various chain lengths and with various molecular weights.

Advantageous polyorganosiloxanes within the context of the present invention are, for example, dimethylpolysiloxane [poly(dimethylsiloxane)], which are available for example under the trade names Abil 10 to 10 000 from Evonik Goldschmidt. Also advantageous are phenylmethylpolysiloxane (INCI: Phenyl Dimethicone, Phenyl Trimethicone), cyclic silicones (octamethylcyclotetrasiloxane and decamethylcyclopentasiloxane), which are also referred to in accordance with INCI as Cyclomethicone, amino-modified silicones (INCI: Amodimethicone) and silicone waxes, e.g. polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are available as various Abil wax grades from Evonik Goldschmidt. However, other silicone oils can also be used advantageously within the context of the present invention, for example cetyldimethicone, hexamethylcyclotrisiloxane, polydimethylsiloxane, poly(methylphenylsiloxane). Silicones that are particularly preferred according to the invention are dimethicone and cyclomethicone.

Suitable oil components are also polycarbonates, as described for example in WO 03/041676, to which reference is expressly made here.

A particularly suitable polycarbonate is that under the INCI name Hydrogenated Dimer Dilinoleyl/Dimethylcarbonate Copolymer, which is available as a commercial product Cosmedia® DC from Cognis GmbH.

The dialkyl carbonates and dialkyl ethers may be symmetrical or asymmetrical, branched or unbranched, saturated or unsaturated and can be prepared by reactions which are sufficiently known from the prior art.

According to the invention, it is also possible to use, inter alia, hydrocarbons, preferably having a chain length of 8 to 40 carbon atoms. They may be branched or unbranched, saturated or unsaturated. Among these, preference is given to branched, saturated $C_8$-$C_{40}$-alkanes. It is possible to use either pure substances or substance mixtures. They are usually substance mixtures of different isomeric compounds. Compositions which have alkenes with 10 to 30, preferably 12 to 20, and particularly preferably 16 to 20, carbon atoms are particularly suitable and, among these, a mixture of alkanes which contains at least 10% by weight of branched alkanes, based on the total amount of the alkanes. They are preferably branched, saturated alkanes. Mixtures of alkanes which contain more than 1% by weight of 5,8-diethyldodecane and/or more than 1% by weight of didecene are particularly suitable.

According to the invention, it is possible to use one oil component or a mixture of two or more oil components.

Component (A)

According to the invention, alkyl and/or alkenyl(oligo) glycoside(s) having 6 to 22 carbon atoms in the alk(en)yl radical are used as component (A). These compounds are known as emulsifiers.

Suitable alkyl and/or alkenyl oligoglycoside(s) (component (A)) are in particular the compounds of the general formula (I):

$$G_m\text{-}R^1 \quad (I)$$

in which G is a sugar radical having 5 or 6 carbon atoms,
$R^1$ is a C6 to C22 alkyl and/or alkenyl radical in acetal bond,
m is an average value from 1 to 10, preferably 1 to 8, in particular 1 to 3, preferably 1.2 to 1.8.

Suitable alkyl and/or alkenyl oligoglycoside(s) (component (A)) are in particular compounds of the general formula (I):

$$G_m\text{-}R^1 \quad (I)$$

in which G is a sugar radical having 5 or 6 carbon atoms,
$R^1$ is a C6 to C22 alkyl and/or alkenyl radical in acetal bond,
m is an average value from 1 to 3, preferably 1.2 to 1.8, and
where at least 50% by weight of the alkyl and/or alkenyl polyglycosides contain a radical $R^1$ with a carbon chain greater than or equal to 12.

According to the invention, component (A) is likewise preferably an alkyl oligoglycoside mixture with a ratio of C12-alkyl radical to C14-alkyl radical of about 7: about 3.

Suitable alkyl and/or alkenyl oligoglycoside(s) (component (A)) are in particular the compounds of the general formula (I)

$$G_m\text{-}R^1 \quad (I)$$

in which G is a sugar radical having 5 or 6 carbon atoms,
$R^1$ is a C6 to C22 alkyl and/or alkenyl radical in acetal bond,
m is an average value from 1 to 10, preferably 1 to 8, in particular 1 to 3, preferably 1.2 to 1.8
where the weight ratio of compounds of the formula (I) in which $R^1$ is a C12 alkyl radical to compounds of the formula (I) in which $R^1$ is a C14 alkyl radical is about 7:about 3.

The alkyl or alkenyl radical R1 can be derived from primary alcohols having 8 to 10 carbon atoms. Typical examples are butanol, caproic alcohol, caprylic alcohol, capric alcohol and undecyl alcohol, and also technical-grade mixtures thereof, as are obtained for example during the hydrogenation of technical-grade fatty acid methyl esters or in the course of the hydrogenation of aldehydes from the Roelen oxo synthesis. In addition, the alkyl or alkenyl radical R1 can also be derived from primary alcohols having 12 to 22, preferably 12 to 16, carbon atoms. Typical examples are lauryl alcohol, isotridecyl alcohol, myristyl alcohol, cetyl alcohol, isocetyl alcohol, palmoleyl alcohol, stearyl alcohol, isostearyl alcohol, ricinoleic alcohol, hydroxystearyl alcohol, dihydroxystearyl alcohol, oleyl alcohol, elaidyl alcohol, petroselinyl alcohol, arachyl alcohol, gadoleyl alcohol, behenyl alcohol, erucyl alcohol, brassidyl alcohol, and technical-grade mixtures thereof.

$C_6$-$C_{22}$-Alkyl mono- and oligoglycosides, their preparation and their use are known from the prior art. Their preparation takes place in particular by reacting glucose or oligosaccharides with primary alcohols having 6 to 22 carbon atoms. As far as the glycoside radical is concerned, either monoglycosides in which a cyclic sugar radical is glycosidically bonded to the fatty alcohol, and also oligomeric glycosides with a degree of oligomerization up to preferably about 8 are suitable. The degree of oligomerization here is a statistical average value based on a homolog distribution customary for such technical-grade products. Products which are available under the name Plantacare® contain a glycosidically bonded $C_{8-16}$-alkyl group on an oligoglucoside radical, the average degree of oligomerization of which is 1 to 2. A preferred example is lauryl glucoside.

The emulsion concentrates can comprise the component (A) in amounts of from 1 to 20% by weight, preferably 10 to 20% by weight, in particular 12 to 18% by weight—based on the total weight of the concentrate.

Component (B)

According to the invention, component (B) is a polyglycerol ester (the term polyglycerin ester is used synonymously). These compounds are known as lipophilic coemulsifiers.

Polyglycerol esters are esters of polyglycerol (synonymous with polyglycerin) with for example fatty acids. The polyglycerols used are polymerization products of glycerol; these are usually mixtures of different polyglycerols, such as e.g. diglycerol, triglycerol, tetraglycerol etc.

In a preferred embodiment of the invention, esters of fatty acids with polyglycerols having an average length of 2 to 12, in particular 2 to 10, particularly preferably 2 to 4, glycerol units are used.

Suitable fatty acids which can be esterified with the polyglycerols are compounds of the general formula (I) $R^1$—COOH, where $R^1$ is a linear or branched, saturated or unsaturated, optionally hydroxy-substituted radical having 6 to 24 carbon atoms, preferably 8 to 20 carbon atoms.

In a preferred embodiment of the invention, a polyglycerol ester which has an HLB value of <10 is used as component (B).

Typical examples of suitable polyglycerol esters are polyglyceryl-4 diisostearate/polyhydroxystearate/sebacate (Isolan® GPS), polyglyceryl-2 dipolyhydroxystearate (trade name Dehymuls® PGPH), polyglycerin-3 diisostearate (trade name Lameform® TGI), polyglyceryl-4 isostearate (trade name Isolan® GI 34), polyglyceryl-3 oleate (trade name e.g. Isolan®GO 33), diisostearoyl polyglyceryl-3 diisostearate (trade name Isolan® PDI), polyglyceryl-3 beeswax (trade name Cera Bellina), polyglyceryl-4 caprate (trade name Polyglycerol Caprate T2010/90), polyglyceryl-3 distearate (trade name Cremophor® GS 32), polyglyceryl polyricinoleate (Admul® WOL 1403), polyglyceryl dimerate isostearate, and mixtures thereof.

According to the invention, preference is given to polyglycerol esters of polyhydroxystearic acid. Polyglyceryl-2 dipolyhydroxystearate is a component (B) preferred according to the invention. This compound is available for example under the trade name Dehymuls®PGPH from Cognis or under the name AEC Polyglyceryl-2 Dipolyhydroxystearate from A & E Connock.

The emulsion concentrates can comprise the component (B) in amounts of 1 to 20% by weight, preferably 5 to 20% by weight, in particular 8 to 18% by weight—based on the total weight of the concentrate.

According to the invention, the ratio of components (A) to (B) is 1:(0.6-0.8). The emulsion concentrates can comprise the components (A) and (B) in total e.g. in amounts of 2 to 40, preferably 10 to 40, in particular 15 to 36, % by weight and particularly preferably 20 to 35% by weight, based on the total weight of the concentrate.

Component (C)—Polyols

Polyols is the term used to refer to polyhydric alcohols, i.e. organic compounds which carry at least 2 alcoholic hydroxyl groups in the molecule. In one embodiment of the invention, the polyols contain 2 to 6 hydroxyl groups per molecule. In one embodiment of the invention, the polyols used are low molecular weight polyhydric alcohols, i.e. compounds which contain 2 to 18, in particular 2 to 10, preferably 2 to 6, carbon atoms.

The polyols according to the invention here are substances different from the components (A), (B) and (D), (E) and (F). i.e. if the emulsion concentrate according to the invention contains an alkyl and/or alkenyl oligoglycoside (A) or a polyglycerol ester (B) or a glyceride (D) or an oil component (E) or (F) which carries at least 2 alcoholic hydroxyl groups in the molecule, these are counted as the corresponding component (A), (B), (D), (E) or (F) and not as component (C).

In a preferred embodiment of the invention, compounds which carry at least 2 hydroxyl groups per molecule and consist of 2 to 18, preferably 2 to 10, in particular 2 to 6, carbon atoms are used as polyols (C).

In a preferred embodiment of the invention, compounds which carry 2 to 6 hydroxyl groups per molecule are used as polyols (C). Particular preference is given to polyols (C) which carry 2 to 6 hydroxyl groups per molecule and consist of 2 to 6 carbon atoms.

Both individual polyols and also mixtures of any desired polyols can be used as polyols (C). In a preferred embodiment, the polyols used are mixtures of at least two, in particular at least three, polyols.

The polyols (C) can also contain further functional groups, in particular amino groups, and/or be modified with nitrogen.

In a preferred embodiment, the polyols contain no further functional groups apart from the hydroxyl groups.

In one embodiment of the invention, the polyols (C) are selected from the group consisting of glycerol, diglycerol, triglycerol, tetraglycerol, alkylene glycols and polyalkylene glycols.

Suitable alkylene glycols are ethylene glycol (=1,2-ethanediol), diethylene glycol (=2,2'-oxydiethanol; HO—$(CH_2)_2$—O—$(CH_2)_2$—OH), triethylene glycol (=2,2'-(ethylenedioxy)diethanol), 1,2-propylene glycol, 1,3-propylene glycol, butylene glycols (=butanediols) such as 1,2-butylene glycol, 1,3-butylene glycol, 1,4-butylene glycol, 2,3-butylene glycol; pentane-1,5-diol; pentane-1,2-diol; meso-pentane-2,4-diol, (2R, 4R)-pentane-2,4-diol; (2S, 4S)-pentane-2,4-diol, hexanediols, such as for example hexylene glycol (=2-methylpentane-2,4-diol), heptanediols, octanediols and decanediols.

Polyalkylene glycols is the term used to refer to predominantly linear, but sometimes also branched, polyethers which are formed from the polycondensation of glycols. The technically important representatives of these polyetherpolyols are the polyethylene glycols, polypropylene glycols, polyethylene/polypropylene glycols, and polytetramethylene glycols and analogous compounds thereof which are produced by ring-opening polymerization of ethylene oxide, propylene oxide or tetrahydrofuran.

Within the context of the invention, particularly preferred polyalkylene glycols are polyethylene glycols and/or polypropylene glycols and/or polyethylene-polypropylene glycols with an average molecular weight from 100 to 1000 daltons.

The preferred polyalkylene glycols conform here to the general formula

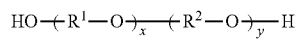

If $R^1$ and $R^2=(CH_2)_2$, the formula refers to polyethylene glycols; if $R^1$ and $R^2=CH_2$—$CH(CH_3)$, the formula refers to polypropylene glycols. If $R^1=(CH_2)_2$ and $R^2=CH_2$—CH($CH_3$), the formula refers to polyethylene/polypropylene glycols.

These compounds are commercially available for example under the INCI name (trade name and manufacturer in brackets):

INCI: PEG-4 (Polyglykol 200 USP, Clariant International; Pluracare E 200, BASF Corp.)

INCI: PEG-12 (Polyglykol 600, Clariant International; Pluracare E 600, BASF Corp.)

INCI: PPG-3 (Newpol PP-200, Sanyo Chemical Industries)

In a further embodiment of the invention, the polyols (c) are selected from the group which is formed by
glycerol, diglycerol, triglycerol, tetraglycerol
alkylene glycols selected from the group consisting of ethylene glycol (=1,2-ethanediol), diethylene glycol (=2,2'-oxydiethanol; HO—$(CH_2)_2$—O—$(CH_2)_2$—O—$(CH_2)_2$—OH), triethylene glycol (=2,2'-(ethylenedioxy)diethanol), 1,2-propylene glycol, 1,3-propylene glycol, butylene glycols (=butanediols) such as 1,2-butylene glycol, 1,3-butylene glycol, 1,4-butylene glycol, 2,3-butylene glycol; pentane-1,5-diol; pentane-1,2-diol; meso-pentane-2,4-diol, (2R, 4R)-pentane-2,4-diol; (2S, 4S)-petane-2,4-diol, hexanediols, such as for example hexylene glycol (=2-methylpentane-2,4-diol), heptanediols, octanediols and decanediols.

polyalkylene glycols with an average molecular weight of from 100 to 1000 daltons technical-grade oligoglycerol mixtures with a degree of autocondensation of from 1.5 to 10, such as for example technical-grade diglycerol mixtures with a diglycerol content of from 40 to 50% by weight;

methanol compounds, such as in particular trimethylolethane, trimethylolpropane, trimethylolbutane, pentaerythritol and dipentaerythritol;

short-chain alkyl glucosides, in particular those having 1 to 5 carbon atoms in the alkyl radical, such as for example methyl and butyl glucoside;

sugar alcohols having 5 to 12 carbon atoms, such as for example sorbitol or mannitol;

sugars having 5 to 12 carbon atoms, such as for example glucose or sucrose;

amino sugars, such as for example glucamine;

dialcohol amines, such as diethanolamine or 2-amino-1,3-propanediol.

In a preferred embodiment of the invention, at least one compound selected from the group consisting of glycerol, 1,2-propylene glycol, sorbitol, butylene glycols and hexylene glycol is used as polyol (C).

The emulsion concentrates can comprise the component (C) in amounts of from 1 to 20, preferably 10 to 20, in particular 12 to 18% by weight—based on the total weight of the concentrate. According to the invention, the weight ratio of components (A), (B) and (C) is 1:(0.6-0.8):(0.9-1.1).

Component (D)—Glycerides

As component (D), according to the invention, glycerides are used which have a melting point of greater than or equal to 20° C., in particular those glycerides which have a melting point of greater than or equal to 30° C. These likewise have a coemulsifier effect. The term glycerides covers esters of carboxylic acids, in particular of fatty acids with glycerol. Depending on the number of acid radicals, a distinction is made between monoacyl glycerols (=monoglycerides), diacyl glycerols (=diglycerides) and triacyl glycerols (=triglcerides). According to the invention, glycerides encompasses monoglycerides, diglycerides and triglycerides and any desired mixtures of these compounds. Monoglycerides and diglycerides are also referred to as partial glycerides or glycerol partial esters.

Typical examples of suitable partial glycerides are mono- and/or diglycerides of C12 to C22 fatty acids with glycerol and technical-grade mixtures thereof. For example, mention may be made of long-chain hydroxy fatty acid monoglycerides, long-chain hydroxy fatty acid diglycerides, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride.

Typical examples of suitable partial glycerides are mono- and/or diglycerides of dicarboxylic acids having 4 to 8 carbon atoms with glycerol, and technical-grade mixtures thereof. Of particular suitability are those partial glycerides which have a melting point of >30° C. For example, mention may be made of tartaric acid monoglyceride, tartaric acid diglyceride, citric acid monoglyceride, citric acid diglyceride, malic acid monoglyceride, malic acid diglyceride, and technical-grade mixtures thereof, which may also contain small amounts of triglyceride in minor amounts from the preparation process.

As component (D), according to the invention, it is possible to use in particular mono- and diglycerides and mixtures of these partial glycerides. The glyceride mixtures which can be used according to the invention include the products Novata® AB and Novata® B (mixture of C12-C18-mono-, di- and triglycerides) and also Cutina® MD or Cutina® GMS (glyceryl stearate) marketed by Cognis GmbH.

In a preferred embodiment of the invention, glycerides of C18 fatty acids are used as components (D). The fraction of glycerol monoesters of C18 fatty acids—based on the total weight of all of the glycerides of C18 fatty acids—is preferably greater than or equal to 90% by weight, preferably greater than or equal to 95% by weight. Suitable C18 fatty acids are in particular mono-, di- or triunsaturated C18 fatty acids. In a preferred embodiment of the invention, glycerides of C18 fatty acids where the fraction of the glycerides with unsaturated C18 fatty acids (based on the total weight of all glycerides of C18 fatty acids) is greater than or equal to 80% by weight, preferably greater than or equal to 90% by weight, are used as component (D).

According to the invention, the component (D) can be present e.g. in a fraction of from about 1 to 10% by weight, preferably about 2 to 8% by weight, based on the emulsion concentrate. According to the invention, the weight ratio of component (A) to component (D) is 4:1 to 1.5:1, in particular 3.5:1 to 2:1.

Aqueous Fraction

The concentrates according to the invention have a water content of less than or equal to 20% by weight, preferably less than or equal to 18% by weight.

Ethoxylated Substances

In a preferred embodiment of the invention, the emulsion concentrates comprise a fraction of ethoxylated substances which is below 10% by weight, in particular below 5% by weight, preferably below 2% by weight, in particular below 1% by weight, based on the emulsion concentrate. In a particularly preferred embodiment of the invention, the emulsion concentrates are free from ethoxylated substances.

Preparation of the Emulsion Concentrates According to the Invention

One way of producing the emulsion concentrates according to the invention is as follows: All of components (A) to (F) are heated together with the water with stirring at 70 to 75° C. for 60 min. The concentrate is then cooled to 30° C. and, if appropriate, the pH is adjusted to 5.0 to 6.0.

Use of the Emulsion Concentrates

The emulsion concentrates according to the invention can be used directly as cosmetic or pharmaceutical preparation. The invention therefore further provides the use of the emulsion concentrates according to the invention as cosmetic or pharmaceutical preparations.

The emulsion concentrates according to the invention are finely divided and very storage-stable, they are therefore very particularly suitable as preprepared emulsion building block which, on account of its free-flowability, is readily suitable for storage and transportation to a processing site with little technical finishing, in order there to produce useful cosmetic and pharmaceutical emulsions, in particular oil-in-water emulsions, with the simplest of means.

Accordingly, the invention provides the use of the emulsion concentrates according to the invention for producing cosmetic or pharmaceutical preparations.

The emulsion concentrate according to the invention is particularly suitable for producing cosmetic or pharmaceutical oil-in-water emulsions. Here, it is possible, for example, to introduce the emulsion concentrate as initial charge and to add the aqueous phase to the initial charge; similarly, the aqueous phase can be introduced as initial charge and the emulsion concentrate can be added to the aqueous initial charge. It is also possible to mix the emulsion concentrate with further lipophilic components, to add this to the initial charge (aqueous phase), or to add the emulsion concentrate optionally mixed with further lipophilic components as initial charge and to add the aqueous phase to this initial charge.

The preparation of the cosmetic or pharmaceutical preparations can take place here without the introduction of further heat.

The lipophilic phase with which the emulsion concentrate is diluted can comprise any desired lipophilic constituents, e.g. lipophilic cosmetic active ingredients. All compounds suitable as component (E) and (F), for example, are suitable as lipophilic phase.

As a rule, 1 to 50, preferably 2 to 30, in particular 4 to 10, % by weight of the emulsion concentrate are used for producing the cosmetic or pharmaceutical preparations.

Cosmetic or Pharmaceutical Preparations

The invention further provides cosmetic or pharmaceutical preparations comprising the following components:
(A) alkyl and/or alkenyl oligoglycoside(s) having 6 to 22 carbon atoms in the alk(en)yl radical,
(B) polyglycerol ester,
(C) polyol(s),
(D) glyceride(s) which have a melting point greater than or equal to 20° C.
(E) oil component(s) liquid at 20° C. and with a polarity of more than 30-40 mN/m and
(F) oil component(s) liquid at 20° C. and with a polarity of 5-30 mN/m,
where
the components (A), (B) and (C) have a weight ratio A:B:C of 1:(0.6-0.8):(0.9-1.1),
the components (A) and (D) have a weight ratio A:D of from 4:1 to 1.5:1,
the components (E) and (F) have a weight ratio E:F of from 1:1 to 1:3, and Surprisingly, it has been found that through the selection of the components and also the ratios according to the invention of the components relative to one another, it is possible to obtain stable, finely divided preparations, in particular oil-in-water emulsions, which can be formulated without ethoxylated substances.

In a preferred embodiment of the invention, the preparations according to the invention are oil-in-water emulsions.

The preparations according to the invention can be produced for example by diluting the emulsion concentrates according to the invention accordingly. In the simplest case, the dilution takes place with water since in so doing the ratios of the components according to the invention are unchanged.

The cosmetic or pharmaceutical preparations usually have an average particle size of below 1 μm, in particular of below 500 nm, preferably of below 250 nm, particularly preferably of below 200 nm.

Further Constituents

Besides the specified constituents, further customary constituents different from the components (A), (B), (C), (D), (E) and (F) may be present in customary fractions in the emulsion concentrates or in the cosmetic and/or pharmaceutical preparations according to the invention. These include e.g. surfactants, preservatives, biogenic active ingredients, thickeners, superfatting agents, stabilizers, polymers, antioxidants, film formers, swelling agents, insect repellents, hydrotropes, solubilizers, perfume oils, dyes, pigments, UV filters etc.

Should the further constituents be water-insoluble, they should be counted in the lipophilic phase. Depending on polarity, they can then be assigned, as appropriate, to component (E) or (F).

The emulsion concentrates according to the invention comprise the further constituents usually in amounts of in total less than or equal to 25% by weight, in particular less than or equal to 20% by weight, particularly preferably below 10% by weight, based on the total weight of the emulsion concentrate.

The cosmetic and/or pharmaceutical preparations according to the invention comprise the further constituents usually in amounts of in total less than or equal to 25% by weight, in particular less than or equal to 20% by weight, particularly preferably below 10% by weight, based on the total weight of the preparation.

Surfactants

Surfactants are amphiphilic substances which are able to dissolve organic, nonpolar substances in water. As a result of their specific molecular structure with at least one hydrophilic molecular moiety and one hydrophobic molecular moiety, they provide for a reduction in the surface tension of water, wetting of the skin, facilitation of soil removal and dissolution, ease of rinsing off and—if desired—for foam regulation.

Surfactants are usually understood as meaning surface-active substances which have an HLB value of greater than 20. Surface-active substances which may be present are anionic, nonionic, cationic and/or amphoteric or zwitterionic surfactants. In surfactant-containing cosmetic preparations, preferably at least one anionic surfactant is present.

The concentrates or preparations according to the invention can comprise the surfactants usually in an amount of from 0 to 40% by weight, preferably 0.05 to 30% by weight, in particular 0.05 to 20% by weight, preferably 0.1 to 15% by weight and in particular 0.1 to 10% by weight, based on the total weight of the concentrates or preparations.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucuronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these can have a conventional homolog distribution, but preferably have a narrowed homolog distribution.

Zwitterionic surfactants is the term used to refer to those surface-active compounds which carry at least one quaternary ammonium group and at least one —$COO^{(-)}$ or —$SO_3^{(-)}$ group in the molecule. Particularly suitable zwitterionic surfactants are the so-called betaines such as the N-alkyl-N,N-dimethylammonium glycinates, for example cocoalkyldimethylammonium glycinate, N-acylaminopropyl-N,N-dimethylammonium glycinate, for example cocoacylaminopropyldimethylammonium glycinate and 2-alkyl-3-carboxymethyl-3-hydroxyethylimidazoline having in each case 8 to 18 carbon atoms in the alkyl or acyl group, and also cocoacylaminoethylhydroxyethyl carboxymethylglycinate. A preferred zwitterionic-surfactant is the fatty acid amide derivative known under the INCI name Cocamidopropyl Betaine.

Likewise suitable, especially as cosurfactants, are ampholytic surfactants. Ampholytic surfactants are understood as meaning those surface-active compounds which, apart from a $C_8$-$C_{18}$-alkyl or acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylamionacetic acids having in each case about 8 to 18 carbon atoms in the alkyl group. Particularly preferred amopholytic surfactants are N-cocoalkylaminopropionate, cocoacylaminoethylaminopropionate and C$_{12-18}$-acylsarcosine.

Typical examples of amphoteric and zwitterionic surfactants are alkylbetaines, alkylamidobetaines, aminopropionates, aminoglycinates, imidazolinium betaines and sulfobetaines. The specified surfactants are exclusively known compounds. With regard to structure and preparation of these substances, reference may be made to the relevant review works in this field. Typical examples of particularly suitable mild, i.e. particularly skin-compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides and/or mixtures thereof with alkyl oligoglucoside carboxylates, fatty acid glucamides, alkylamidobetaines, amphoacetals and/or protein fatty acid condensates, the latter preferably based on wheat proteins or salts thereof.

Anionic surfactants are characterized by a water-solubilizing, anionic group such as e.g. a carboxylate, sulfate, sulfonates or phosphate group and a lipophilic radical. Skin-compatible anionic surfactants are known to the person skilled in the art in a large number from relevant handbooks and are commercially available. These are in particular alkyl sulfates in the form of their alkali metal, ammonium or alkanolammonium salts, alkyl ether sulfates, alkyl ether carboxylates, acyl isethionates, acyl sarcosinates, acyltaurines with linear alkyl or acyl groups having 12 to 18 carbon atoms, and sulfosuccinates and acyl glutamates in the form of their alkali metal or ammonium salts.

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride(ether)sulfates, fatty acid amide(ether)sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acryl tartrates, acyl glutamates and acyl aspartates, alkyl oligoglucoside sulfates, protein fatty acid condensates (in particular wheat-based vegetable products) and alkyl (ether)phosphates. If the anionic surfactants contain polyglycol ether chains, these can have a conventional homolog distribution, but preferably have a narrowed homolog distribution.

Cationic surfactants which can be used are in particular quaternary ammonium compounds. Preference is given to ammonium halides, in particular chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Furthermore, the very readily biodegradable quaternary ester compounds, such as, for example, the dialkylammonium methosulfates and methylhydroxyalkyldialkoyloxyalkylammonium methosulfates sold under the trade name Stepantex® and the corresponding products of the Dehyquart® series can also be used as cationic surfactants. The term "ester quats" is generally understood as meaning quaternized fatty acid triethanolamine ester salts. These can impart a particular soft feel to the preparations according to the invention. They are known substances which are prepared by the relevant methods of organic chemistry. Further cationic surfactants which can be used according to the invention are the quaternized protein hydrolysates.

Suitable preservatives are, for example, phenoxyethanol, ethylhexylglycerol, dicaprylyl glycol, formaldehyde solution, parabens, petanediol, mixtures of phenoxyethanol and ethylhexylglycerol (as are available for example under the trade name Euxyl PE 9010), or sorbic acid, and also the silver complexes known under the name Surfacine® and the other substance classes listed in Annex 6, part A and B of the Cosmetics Ordinance.

In a preferred embodiment of the invention, the preservative is selected from the group consisting of phenoxyethanol, formaldehyde solution, parabens, organic acids and mixtures thereof, optionally in combination with pentanediol and/or ethylhexyl glycerol or octanediol and ethylhexyl glycerol (trade name Sensiva SC 10).

In a preferred embodiment of the invention, the concentrates or preparations according to the invention comprise at least one compound selected from vitamins, allantoin, bisabolol and plant extracts as biogenic active ingredient.

In a preferred embodiment of the invention, the concentrates or preparations according to the invention comprise, as biogenic active ingredient, at least one compound selected from tocopherol, tocopherol acetate, tocopherol palmitate, ascorbic acid, (deoxy)ribonucleic acids and fragmentation products thereof, β-glucans, retinol, bisabolol, allantoin, phytantriol, panthenol, AHA acids, amino acids, ceramides, pseudoceramides, essential oils, plant extracts, such as e.g. aloe vera, prunus extract, bambara nut extract and vitamin complexes and mixtures thereof.

In one embodiment of the invention, the concentrates or preparations according to the invention comprise at least one thickener as further constituent.

Suitable thickeners are, for example, Aerosil grades (hydrophilic silicas), polysaccharides, in particular xanthan gum, guar guar, agar agar, alginates and tyloses, carboxymethylcellulose and hydroxyethyl- and hydroxypropylcellulose, polyvinyl alcohol, polyvinylpyrrolidone and bentonites, such as e.g. Bentone® Gel VS-5PC (Rheox).

Suitable insect repellents are, for example, N,N-diethyl-m-toluamide, 1,2-pentanediol or ethyl 3-(N-n-butyl-N-acetylamino)propionate, which is sold under the name Insect Repellent® 3535 by Merck KGaA, and also butylacetylaminopropionates.

Perfume oils which may be mentioned are mixtures of natural and synthetic fragrances. Natural fragrances are extracts from flowers, stems and leaves, fruits, fruit peels, roots, woods, herbs and grasses, needles and branches, resins and balsams. Also suitable are animal raw materials, such as for example civet and castoreum, and also synthetic fragrance compounds of the ester, ether, aldehyde, ketone, alcohol and hydrocarbon types.

The term pigment covers particles of any shape, which are white or colored, organic or inorganic, are insoluble in the preparations, and serve the purpose of coloring the preparation. In one preferred embodiment, inorganic pigments are used, particular preference being given to metal oxides.

Examples of inorganic pigments which may be mentioned are: titanium dioxide, optionally surface-coated, zirconium or cerium oxides and zinc, iron (black, yellow or red) and chromium oxides, manganese violet, ultramarine blue, chromium hydrates and iron(III) blue, metal powders such as aluminum powder or copper powder.

In a preferred embodiment of the invention, the pigment is selected from the inorganic pigments, preferably from the metal oxides. In one preferred embodiment, the pigment is selected from the group consisting of titanium dioxide, zinc oxide, iron oxide and mixtures thereof. The pigments can be present either individually or in mixtures. Within the context of the present invention, preference is given to pigment mixtures of white pigments (e.g. kaolin, titanium dioxide or zinc oxide) and inorganic colored pigments (e.g. iron oxide pigments, chromium oxides), where the pigments may be present in coated or uncoated form. Among the colored pigments, iron oxides are particularly preferred.

Within the context of the present invention, the pigment(s) may also advantageously be selected from the group of the effect pigments, which impart to the cosmetic preparation, as well as the pure color, an additional property—such as e.g. angular dependence of the color (flop), luster (not surface luster) or texture. According to the invention, such effect pigments are used advantageously in addition to one or more white pigments and/or colored pigments.

The most important group of effect pigments is that of the luster pigments, which, according to DIN 55944: 2003-11, include the metal effect pigments and the pearlescent pigments. Some specific effect pigments cannot be assigned to these two groups, e.g. graphite platelets, iron oxide platelets and micronized titanium dioxide, where micronized titanium dioxide does not give a luster effect, but an angle-dependent light-scattering effect. The luster pigments according to DIN 55943: 2001-10 are predominantly effect pigment platelets. Oriented in parallel, luster pigments exhibit a characteristic luster. The visual effect of luster pigments is based on the directed reflection on metallic particles (metal effect pigments), on transparent particles with a high refractive index (pearlescent pigments) or on the phenomenon of interference (interference pigments) (DIN 55944: 2003-11).

Examples of standard commercial effect pigments preferred according to the invention are: Timiron and #174; from Merck, Iriodin and #174; from Merck (pearlescent and color luster pigments for decorative technical applications), Xirallic and #174; from Merck (color-intense crystal effect pigments).

In addition, the concentrates or preparations according to the invention can also advantageously comprise organic colored pigments, i.e. organic dyes which are practically insoluble in the preparation. According to DIN 55944: 1990-04, organic pigments can be divided according to chemical aspects into azo pigments and polycyclic pigments, and also according to color aspects into colored or black pigments. Organic white pigments are of practical significance. Within the context of the present invention, the pigments may advantageously also be used in the form of commercially available oily or aqueous predispersions.

It is also possible for the concentrates or preparations according to the invention to comprise one or more dyes.

The dyes may be either of synthetic or natural origin. A list of suitable dyes can be found in EP 1 371 359 A2, p. 8, l. 25-57, p. 9 and p. 10 and also p. 11, l. 1 to 54, to which reference is hereby explicitly made.

Suitable dyes and pigments are in particular the dyes and pigments approved according to Annex IV of the Commission Directive (in the version: Commission Directive 2007/22/EC of 17 Apr. 2007 amending Council Directive 76/768/EEC, concerning cosmetic products, for the purposes of adapting Annexes IV and VI thereto to technical progress), to which reference is hereby explicitly made.

According to the invention, suitable UV photoprotective filters are organic substances (photoprotective filters) that are crystalline or liquid at room temperature and which are able to absorb ultraviolet rays and release the absorbed energy again in the form of longer-wave radiation, e.g. heat. UV filters may be oil-soluble or water-soluble. Typical oil-soluble UV-B filters or broad-spectrum UV A/B filters to be mentioned are, for example:

3-benzylidenecamphor or 3-benzylidenenorcamphor (Mexoryl SDS 20) and derivatives thereof, e.g. 3-(4-methylbenzylidene)camphor as described in EP 0693471 B1

3-(4'-trimethylammonium)benzylidenebornan-2-one methyl sulfate (Mexoryl SO)

3,3'-(1,4-phenylenedimethine)bis(7,7-dimethyl-2-oxobicyclo[2.2.1]heptane-1-methanesulfonic acid) and salts (Mexoryl SX)

3-(4'-sulfo)benzylidenebornan-2-one and salts (Mexoryl SL)

polymer of N-[2 (and 4)-(2-oxoborn-3-ylidene-methyl)benzyl]acrylamide (Mexoryl SW)

2-(2H-benzotriazol-2-yl)-4-methyl-6-(2-methyl-3-(1,3,3,3-tetramethyl-1-(trimethylsilyloxy)disiloxanyl)propyl)phenol (Mexoryl SL)

4-aminobenzoic acid derivatives, preferably 2-ethylhexyl 4-(dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl 4-methoxybenzmalonate;

triazine derivatives, such as e.g. 2,4,6-trianilino(p-carbo-2'-ethyl-1'-hexyloxy)-1,3,5-triazine and 2,4,6-tris[p-(2-ethylhexyloxycarbonyl)anilino]-1,3,5-triazine (Uvinul T 150) as described in EP 0818450 A1 or bis(2-ethylhexyl) 4,4'-[(6-[4-((1,1-dimethylethyl)aminocarbonyl)phenylamino]-1,3,5-triazine-2,4-diyl)diimino]bisbenzoate (Uvasorb® HEB);

2,2-(methylenebis(6-(2H-benzotriazol-2-yl)-4-(1,1,3,3-tetramethylbutyl)phenol) (Tinosorb M);

2,4-bis[4-(2-ethylhexyloxy)-2-hydroxyphenyl]-6-(4-methoxyphenyl)-1,3,5-triazine (Tinosorb S);

propane-1,3-diones, such as e.g. 1-(4-tert-butylphenyl)-3-(4'-methoxyphenyl)propane-1,3-dione;

ketotricyclo(5.2.1.0)decane derivatives, as described in EP 0694521 B1;

dimethicodiethyl benzalmalonates (Parsol SLX).

Suitable Water-Soluble UV Filters are:

2-phenylbenzimidazole-5-sulfonic acid and the alkali metal, alkaline earth metal, ammonium, alkylammonium, alkanolammonium and glucammonium salts thereof;

2,2-(1,4-phenylene)bis(1H-benzimidazole-4,6-disulfonic acid, monosodium salt) (Neo Heliopan AP)

sulfonic acid derivatives of benzophenones, preferably 2-hydroxy-4-methoxybenzophenone-5-sulfonic acid and its salts;

sulfonic acid derivatives of 3-benzylidenecamphor, such as e.g. 4-(2-oxo-3-bornylidenemethyl)benzenesulfonic acid and 2-methyl-5-(2-oxo-3-bornylidene)sulfonic acid and salts thereof.

Suitable typical UV-A filters are in particular derivatives of benzoylmethane, such as for example 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds, as described in DE 19712033 A1 (BASF) and benzoic acid, 2-[4-(diethylamino)-2-hydroxybenzoyl], hexyl ester (Uvinal® A plus).

The UV-A and UV-B filters can of course also be used in mixtures. Particularly favorable combinations consist of the derivatives of benzoylmethane, e.g. 4-tert-butyl-4'-methoxy-dibenzoylmethane (Parsol® 1789) and 2-ethylhexyl 2-cyano-3,3-phenylcinnamate(octocrylene) in combination with esters of cinnamic acid, preferably 2-ethylhexyl 4-methoxy-cinnamate and/or propyl 4-methoxycinnamate and/or isoamyl 4-methoxycinnamate. Combinations of this type are advantageously combined with water-soluble filters such as e.g. 2-phenylbenzimidazole-5-sulfonic acid and alkali metal, alkaline earth metal, ammonium, alkylammonium, alkanola-mmonium and glucammonium salts thereof.

Suitable UV photoprotective filters are in particular the substances approved according to Annex VII of the Commission Directive (in the version Commission Directive 2005/9/EC of 28 Jan. 2005 amending Council Directive 76/768/EEC, concerning cosmetic products, for the purposes of adapting Annexes VII thereof to technical progress), to which reference is hereby explicitly made.

Besides the specified soluble substances, insoluble photo-protective pigments are also suitable for this purpose, namely finely disperse metal oxides and salts. Examples of suitable metal oxides are, in particular, zinc oxide and titanium dioxide and also oxides of iron, zirconium, silicon, manganese, aluminum and cerium, and mixtures thereof. Salts which can be used are silicates (talc), barium sulfate or zinc stearate. The oxides and salts are used in the form of the pigments for skincare and skin-protecting emulsions and also for decorative cosmetics. The particles should have an average diameter of less than 100 nm, preferably between 5 and 50 nm and in particular between 15 and 30 nm. They can have a spherical shape, although it is also possible to use those particles which have an ellipsoidal shape or a shape which deviates in some other way from the spherical configuration. The pigments can also be present in surface-treated form, i.e. hydrophilized or hydrophobized. Typical examples are coated titanium dioxides, such as e.g. titanium dioxide T 805 (Degussa) or Eusolex® T, Eusolex® T-2000, Eusolex® T-Aqua, Eusolex® AVO, Eusolex® T-ECO, Eusolex® T-OLEO and Eusolex® T-S (Merck). Typical examples are zinc oxides, such as e.g. zinc oxide neutral, zinc oxide NDM (Symrise) or Z-Cote® (BASF) or SUNZnO-AS and SUNZnO-NAS (Sunjun Chemical Co. Ltd.). Suitable hydrophobic coatings here are primarily silicones and specifically trialkoxyoctylsilanes or simethicones. In sunscreen compositions, preference is given to using so-called micropigments or nanopigments. Preference is given to using micronized zinc oxide. Further suitable UV photoprotective filters can be found in the review by P. Finkel in SÖFW-Journal 122, 8/1996, pp. 543-548 and Parf. Kosmo. 80$^{th}$ volume, No. 3/1999, p. 10 to 16.

Besides the two aforementioned groups of primary photo-protective substances, it is also possible to use secondary photoprotective agents of the antioxidant type, which interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocaninic acid) and derivatives thereof, peptides such as D,L-carnosine, D-carnosine, L-carnosine and derivatives thereof (e.g. anserine), carotenoids, carotenes (e.g. alpha-carotene, beta-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to mol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. gamma-linolenic acid, linolic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxy-toluene, butylhydroxyanisole, nordihydroguaicic acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO4), selenium and derivatives thereof (e.g. selenomethionine), stilbene and derivatives thereof (e.g. stilbene oxide, trans-stilbene oxide) and the derivatives (salts, esters, ethers, sugars, nucleotides, nucleosides, peptides and lipids) suitable according to the invention of these specified active ingredients.

In one embodiment of the invention, the concentrates or preparations according to the invention comprise at least one deodorizing active ingredient as further constituent.

Deodorizing active ingredients counteract, mask or eliminate body odors. Body odors are formed as a result of the action of skin bacteria on apocrine perspiration, whereupon unpleasant degradation products are formed. Accordingly, suitable deodorizing active ingredients are, inter alia, antimicrobial agents, enzyme inhibitors, odor absorbers or odor maskers.

Metal salts of fatty acids, such as e.g. magnesium, aluminum and/or zinc stearate and/or ricinoleate, can be used as stabilizers.

The further constituents of the concentrates or preparations (such as e.g. preservatives, cosmetic active ingredients such as e.g. DHA—dihydroxyacetone—, UV filters etc.) are added either via the water phase or via the lyphophilic phase, depending on their solubility.

The aqueous phase with which the emulsion concentrate is diluted, or the aqueous phase of the cosmetic or pharmaceutical preparations according to the invention, can comprise, in dissolved form, various water-soluble constituents, e.g. water-soluble cosmetic active ingredients, water-soluble proteins or protein degradation products, preservatives, dyes, fragrances, magnesium salts or other customary water-soluble components. Preferably, the aqueous, continuous phase comprises a water-soluble, natural or synthetic polymer which improves the cosmetic properties of the emulsions by increasing the viscosity. A particularly effective combination of hydrocolloids for improving the cosmetic properties of such emulsions is a mixture of nonionic cellulose ethers, e.g. hydroxypropylcellulose and crosslinked acrylic acid polymers, as are available e.g. under the trade name Carbopol® (cf. DE 3521713 A1). Moreover, particularly suitable polymers are known under the trade names (Cosmedia® ATH, Cosmedia® SP, Cosmedia® CHT (E), Ultragel™ 300, Rheocare™ TTA, Rheocare™ TTN, Rheocare™ TTN-2, Cosmedia®Triple C, Rheocare™C plus).

Use for the Treatment of Substrates and Treated Substrates

The emulsion concentrates according to the invention and also the cosmetic or pharmaceutical preparations according to the invention are suitable in particular for the treatment of substrates.

The invention therefore further provides the use of the emulsion concentrates according to the invention or of the preparations according to the invention for treating substrates, in particular papers, nonwovens and wovens. Included here according to the invention are all types of paper, nonwovens and wovens which are known to the person skilled in the art, and products which can be produced therefrom, such as, for example, toilet paper, paper tissues, tissues, wipes, cotton wool, cotton wool pads, make-up removers, tampons, sanitary napkins, panty liners, diapers, baby care wipes, baby cleansing wipes, textiles, etc.

The term treatment includes here every type of application of an emulsion concentrate according to the invention and also of a cosmetic or pharmaceutical preparation according to the invention to at least one side of the substrate. Of suitability for this are all relevant known methods, with the help of which liquids can be applied to more or less solid surfaces. By way of example, mention may be made of: impregnation, saturation, coating, spraying (on), immersion, finishing, stripping etc. The treatment can be undertaken here at room temperature or under the action of heat. After the compositions have been applied, a short drying step can follow.

The emulsion concentrates and also the preparations are particularly suitable for application to substrates, such as, for example, papers, wipes, textiles and cotton wool products which are used in the baby care and baby hygiene sector and also in the field of make-up removal, in particular of eye make-up removal, in the area of women's hygiene (tampons, sanitary napkins, panty liners) and in the area of body hygiene (toilet paper, moist toilet paper).

The invention further provides a substrate which comprises at least the following constituents:
(A) alkyl and/or alkenyl oligoglycoside(s) having 6 to 22 carbon atoms in the alk(en)yl radical,
(B) polyglycerol ester,
(C) polyol(s),
(D) glyceride(s) which have a melting point greater than or equal to 20° C.
(E) oil component(s) liquid at 20° C. and with a polarity of more than 30-40 mN/m and
(F) oil component(s) liquid at 20° C. and with a polarity of 5-30 mN/m,
where
the components (A), (B) and (C) have a weight ratio A:B:C of 1:(0.6-0.8):(0.9-1.1),
the components (A) and (D) have a weight ratio A:D of from 4:1 to 1.5:1,
the components (E) and (F) have a weight ratio E:F of from 1:1 to 1:3, and The substrates according to the invention are obtainable, for example, by applying an emulsion concentrate according to the invention or a preparation according to the invention to a substrate.

The substrates according to the invention can be used, for example, as care or cleansing wipes. In this connection, applications both in the field of skin care or cleansing (in particular baby care or cleansing) are possible. For example, mention may be made of care or cleansing wipes for facial skin (so-called facial tissues, make-up removal wipes/make-up removal etc.), freshening wipes for the skin, antibacterial and/or deodorizing wipes, products for intimate care; such as for example tampons, sanitary napkins, panty liners, intimate care wipes), dry or moist toilet paper, incontinence products, self-tanning wipes or so-called insect repellent wipes. Using the preparations according to the invention, it is possible to apply the constituents required for the particular application (e.g. deodorizing active ingredients or oil-soluble care components) to the substrate. The substrates treated in this way are further suitable for the disinfection of skin and hair.

The invention therefore further provides the use of a substrate according to the invention for the cleaning and/or care of skin and hair.

The invention therefore further provides the use of a substrate according to the invention for the disinfection of skin and hair.

Suitable substrates are in principle any carriers which permit the absorption of the composition and/or its constituents. Suitable substrates are, for example, tissue papers and/or tissue fabrics and/or tissue wipes (referred to below as tissue wipes). These may be of single-ply or multi-ply construction. As a rule, the papers have a weight per square meter of 10 to 65, preferably 15 to 30 g and a density of 0.6 g/cm or less. Examples of tissue papers are toilet papers, paper tissues, face cleansing wipes, make-up remover wipes, freshening wipes, household wipes and the like. Besides the paper-based tissues, corresponding tissue fabrics produced from fiber or fleece material are also suitable.

According to the invention, multi-ply tissue wipes are preferred as substrate. In particular, preference is given to those tissue wipes which have an impermeable and/or partly permeable barrier layer between the individual plies. The partly permeable barrier layer may take the form, for example, of a semipermeable membrane. With wipes of this type, two or more emulsion concentrates (if appropriate after prior dilution) can be applied to a wipe. This may be especially preferred in order to bring about cleansing by means of the composition applied to the wipe using one side of the wipes. The other side can then be used for subsequent rubbing, for example for the purpose of drying or, if appropriate, for applying a care active ingredient to the skin.

Furthermore, it may be very particularly preferred according to the invention if the wipes consist of at least three plies of tissue wipe treated with emulsion concentrates (if appropriate after prior dilution). Advantageously then there is one ply of wipe in the form of a semipermeable membrane in each case between at least two plies of treated wipe. The semipermeable membrane here is permeable in the direction of the outer wipe plies. Consequently, in the interior, it is possible to apply, for example, an emulsion concentrate (if appropriate after prior dilution) to the innermost layer, which is either not miscible and/or not stable with the emulsion concentrate applied to the outer side. As a result, it becomes possible to offer "two in one wipes" for cleansing and care. The invention naturally includes differently colored configurations of the wipe plies. Furthermore, the teaching according to the invention also encompasses the construction of the wipes from two or more materials, particularly with regard to the absorbency and permeability of the different wipe plies.

Suitable substrates are furthermore, for example, textile fibers, both made of natural fibers such as e.g. cellulose, silk, wool, regenerated cellulose (viscose, rayon), cellulose derivatives, and also textile fibers made of synthetic fibers such as e.g. polyester, polypropylene, polyethylene terephthalate, polyamide, polyolefin, polyacrylonitrile fibers or mixtures of such fibers. These fibers may be woven or nonwoven.

The substrates according to the invention can be produced by methods known to the person skilled in the art. The application of the emulsion concentrates according to the invention or of the preparations according to the invention takes place by treating the substrates by methods known to the person skilled in the art.

The emulsion concentrates according to the invention or the preparations according to the invention can be diluted before treating the substrates and, if appropriate, the substrate obtained can then be dried.

EXAMPLES

The following examples serve to illustrate the present invention in more detail.

The emulsion concentrates listed in Tab. 1 were prepared as follows.

Alkyl and/or alkenyl oligoglycosides (A), polyglycerol ester (B) together with the polyol (C), glyceride (D), oil-soluble components (E) and (F) and water were heated with stirring to 70-75° C. for 60 min. The mixture was then cooled with stirring to 30° C. and, if appropriate, the pH was adjusted to pH 5.0-6.0.

Table 1 shows the composition of the emulsion concentrates and their viscosities. The viscosity was determined both at room temperature (23° C.) and also at 15° C. using a Brookfield rotary viscometer (model RVF, spindle 5, 10 rpm). It was found that both good storage stability and also good viscosity properties were achieved, both at room temperature and also at lower temperature, while retaining the parameters according to the invention.

Also shown are the stability results of the dilutions with water and their particle size. The dilutions according to the invention of the emulsion concentrates are stable upon storage.

TABLE 1

Composition and results of emulsion concentrates according to the invention (all data in % by wt, based on the weight of the concentrate)

| | Component INCI | Ex. 1 | Ex. 2 | Ex. 3 | Ex. 4 |
|---|---|---|---|---|---|
| (A) | Lauryl glucoside | 15.0 | 13.75 | 16.25 | 13.75 |
| (B) | Polyglyceryl-2 dipolyhydroxystearate | 11.25 | 10.35 | 12.15 | 10.35 |
| (C) | Glycerin | 15.0 | 13.75 | 16.25 | 13.75 |
| (D) | Glyceryl polyhydroxystearate | 3.75 | 3.4 | 4.1 | 3.4 |
| (D) | Glyceryl oleate | 3.0 | 3.0 | 3.0 | 3.0 |
| (E) | Dicaprylyl ether | 13.0 | 13.0 | — | — |
| | Cetearyl alcohol | — | — | — | — |
| (E) | Dicaprylyl carbonate | — | — | 8.0 | — |
| (E) | Propylheptyl caprylate | — | — | — | 13.0 |
| (F) | Caprylic/capric triglyceride | 24.0 | 29.0 | 24.0 | 29.0 |
| (F) | Olus | — | — | — | — |
| | Citric acid (for the pH adjustment) | | | | |
| | Water | 15.0 | 13.75 | 16.25 | 13.75 |
| | Viscosity (RT), mPas * s | 3600 | 2000 | 6400 | 1200 |
| | Viscosity (15° C.), mPas * s | 6400 | 4800 | 14000 | 10000 |
| | Particle size, 5% dilution average value (Coulter LS), nm | 81 | 82 | 79 | 83 |
| | Appearance 5% aqueous dilution | transparent | transparent | transparent | transparent |

TABLE 2

Ratios of components relative to one another.

| Example | Ratio (A):(B):(C) | Ratio (A):(D) | Ratio (E):(F) |
|---|---|---|---|
| 1 | 1:0.75:1 | 2.2:1 | 1:1.3 |
| 2 | 1:0.75:1 | 2.1:1 | 1:2.2 |
| 3 | 1:0.75:1 | 2.3:1 | 1:3 |
| 4 | 1:0.75:1 | 2.1:1 | 1:2.2 |

TABLE 3

Emulsion concentrate - aqueous dilutions. All data in % by weight of active substance, based on the total weight of the preparation.

| Component | 1 | 2 | 3 | 4 | 5 | 6 | 7 | 8 | 9 |
|---|---|---|---|---|---|---|---|---|---|
| Emulsion concentrate as in Ex. 1* | 5.0 | 4.0 | 7.5 | 3.5 | 6.5 | 2.0 | 7.5 | 9.0 | 5.5 |
| Euxyl ® K 300 | | | | 0.8 | | | 0.8 | | |
| Nipaguard ®BPX | | | 0.5 | | | | | | |
| Soidum benzoate | 0.5 | | | | | | | | 0.5 |
| Potassium sorbate | | | | | | | | | 0.2 |
| EuxylPE ®9010 | | | | | | 1.0 | | | |
| Nipaguard ®P05 | | 1.0 | | | 1.0 | | | 1.0 | |
| Sensiva SC ®10 | 0.2 | | | | | 0.1 | | | |
| Herbalia ®Green Tea (Camellia sinensis and silica) | | | | | | 0.05 | | | |
| Cosmedia ®SP | | | 0.3 | 0.2 | | | | | |
| Melhydran ® LS 4420 | | | | 0.5 | | | | | |
| Lactolan ® LS 5879 | | | | 0.5 | | | | | |
| Copherol ® 1250 C | | | | | 0.4 | | | | |
| Dihydroxyacetone (DHA) | | | | | | | | | 2.0 |
| Insect repellent 3535 ® | | | | | | | | 10.0 | |

TABLE 3-continued

Emulsion concentrate - aqueous dilutions. All data in % by weight of active substance, based on the total weight of the preparation.

| Component | 1 | 2 | 3 | 4 | 5 | 6 | 7 | 8 | 9 |
|---|---|---|---|---|---|---|---|---|---|
| Eusolex ® OCR | | | | | | | 1.0 | | |
| Eusolex ® 9020 | | | | | | | 0.3 | | |
| Myritol ® 318 | | | | 0.1 | | | | | |
| Perfume | | 0.1 | 0.2 | | 0.3 | | 0.1 | | 0.25 |
| Water | | | | | ad 100 | | | | |
| pH of the dilution (if necessary adjust with pH adjuster) | 4.2-5.0 | 6.0-7.0 | 4.2-5.0 | 6.0-6.5 | 6.0-6.5 | 6.0-6.5 | 6.0-6.5 | 6.0-6.5 | 3.5-4.0 |

*Alternatively, instead of the emulsion concentrate as in Ex. 1, it is also possible to use those from Ex. 2, Ex. 3 or Ex. 4.

Commercial Products Used:

Euxyl®K 300 INCI: Phenoxyethanol, Methylparaben, Ethylparaben, Propylparaben, Butylparaben, Isobutylparaben; Nipaguard®BPX INCI: Phenoxyethanol, Methylparaben, Propylparaben, 2-Bromo-2-Nitro-propane-1,3-Diol; EuxylPE® 9010 INCI: Phenoxyethanol, Ethylhexylglycerin; Nipaguard®PO5 INCI: Phenoxyethanol, Piroctone Olamine; Sensive® SC10 INCI: Caprylyl Glycol, Ethylhexylglycerin; Cosmedia®SP INCI: Sodium Polyacrylate; Melhydran® LS 4420 INCI: Honey extract; Lactolan® LS 5879 INCI: Hydrolyzed Milk Protein; Copherol® 1250 C INCI: Tocopheryl Acetate; Insect Repellent 3535® INCI: Ethyl Butylacetylaminopropionate; Eusolex® OCR INCI: Octocrylene; Eusolex® 9020 INCI: Butyl Methoxydibenzoylmethane; Myritol$^g$ 318 INCI: Caprylic/Capric Triglyceride.

The invention claimed is:

1. An emulsion concentrate comprising:
    (A) at least one alkyl and/or alkenyl oligoglycoside having 6 to 22 carbon atoms in the alk(en)yl radical,
    (B) polyglycerol ester,
    (C) at least one polyol,
    (D) at least one glyceride having a melting point greater than or equal to 20° C.
    (E) at least one oil component liquid at 20° C. and with a polarity of more than 30-40 mN/m and
    (F) at least one oil component liquid at 20° C. and with a polarity of 5-30 mN/m,
    the components (A), (B) and (C) have a weight ratio A:B:C of 1:(0.6-0.8):(0.9-1.1),
    the components (A) and (D) have a weight ratio A:D of from 4:1 to 1.5:1,
    the components (E) and (F) have a weight ratio E:F of from 1:1 to 1:3, and
    the water fraction is less than or equal to 20% by weight, based on the total weight of the emulsion concentrate,
    wherein the emulsion concentrate has a viscosity at 15° C. of less than 30,000 mPa*s.

2. The emulsion concentrate of claim 1, wherein the at least one alkyl and/or alkenyl oligoglycoside have a general formula (I)

$$G_m\text{-}R^1 \quad (I)$$

in which where G is a sugar radical having 5 or 6 carbon atoms,
$R^1$ is a C6 to C22 alkyl and/or alkenyl radical in acetal bond,
m is an average value from 1 to 10.

3. The emulsion concentrate of claim 1, wherein the polyglycerol ester is a polyglycerol ester of a polyhydroxystearic acid.

4. The emulsion concentrate of claim 1, wherein the at least one polyol has 2 to 6 hydroxyl groups.

5. The emulsion concentrate of claim 4, wherein the polyol has 2 to 18 carbon atoms.

6. The emulsion concentrate of claim 1, wherein the at least one glyceride comprises glycerides of C18 fatty acids.

7. The emulsion concentrate of claim 1, wherein there is less than 10% by weight ethoxylated substances.

8. A cosmetic or pharmaceutical preparation comprising the emulsion concentrate of claim 1.

9. A method of making a cosmetic or pharmaceutical preparation comprising an oil-in-water emulsion including the emulsion concentrate of claim 1.

10. A cosmetic or pharmaceutical preparation comprising the emulsion concentrate of claim 1.

11. A method of treating a substrate comprising applying the emulsion concentrate of claim 1 to the substrate.

12. A substrate comprising:
    (A) at least one alkyl and/or alkenyl oligoglycoside having 6 to 22 carbon atoms in the alk(en)yl radical,
    (B) polyglycerol ester,
    (C) at least one polyol,
    (D) at least one glyceride having a melting point greater than or equal to 20° C.
    (E) at least one oil component liquid at 20° C. and with a polarity of more than 30-40 mN/m and
    (F) at least one oil component liquid at 20° C. and with a polarity of 5-30 mN/m,
    components (A), (B) and (C) have a weight ratio A:B:C of 1:(0.6-0.8):(0.9-1.1),
    components (A) and (D) have a weight ratio A:D of from 4:1 to 1.5:1,
    components (E) and (F) have a weight ratio E:F of from 1:1 to 1:3, and
    the water fraction is less than or equal to 20% by weight, based on the total weight of the emulsion concentrate,
    wherein the emulsion concentrate has a viscosity at 15° C. of less than 30,000 mPa*s.

13. A method of bodycare or cleansing comprising using the substrate of claim 12.

14. The emulsion concentrate of claim 2, wherein m has an average value from 1.2 to 1.8.

15. The emulsion concentrate of claim 6, wherein the glycerides of C18 fatty acids have a fraction of glycerol monoester greater than or equal to 90% by weight based on the weight of all of the glycerides of C18 fatty acids.

16. The emulsion of claim 7, wherein there is less than 5% by weight ethoxylated substances.

17. The substrate of claim 12, wherein the substrate is paper, a nonwoven product or a woven product.

18. An article comprising:
a substrate with an emulsion concentrate thereon, the emulsion concentrate comprising:
(A) at least one alkyl and/or alkenyl oligoglycoside having 6 to 22 carbon atoms in the alk(en)yl radical,
(B) polyglycerol ester,
(C) at least one polyol,
(D) at least one glyceride having a melting point greater than or equal to 20° C.
(E) at least one oil component liquid at 20° C. and with a polarity of more than 30-40 mN/m and
(F) at least one oil component liquid at 20° C. and with a polarity of 5-30 mN/m,
where components (A), (B) and (C) are present in a weight ratio A:B:C of 1:(0.6-0.8):(0.9-1.1),
components (A) and (D) are present in a weight ratio A:D of from 4:1 to 1.5:1,
components (E) and (F) are present in a weight ratio E:F of from 1:1 to 1:3, and
the water fraction is less than or equal to 20% by weight, based on the total weight of the emulsion concentrate,
wherein the emulsion concentrate has a viscosity at 15° C. of less than 30,000 mPa*s.

19. The article of claim 18, wherein the emulsion concentrate is part of an oil-in-water emulsion.

* * * * *